(12) United States Patent
Abe

(10) Patent No.: US 6,673,061 B2
(45) Date of Patent: Jan. 6, 2004

(54) LASER TREATMENT APPARATUS

(75) Inventor: Hitoshi Abe, Okazaki (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 10/055,920

(22) Filed: Jan. 28, 2002

(65) Prior Publication Data

US 2002/0103480 A1 Aug. 1, 2002

(30) Foreign Application Priority Data

Feb. 1, 2001 (JP) .......................... 2001-025004

(51) Int. Cl.⁷ .............................................. A61F 9/008
(52) U.S. Cl. ............................... 606/4; 606/11; 606/18
(58) Field of Search .......................... 606/4–6, 11, 18

(56) References Cited

U.S. PATENT DOCUMENTS

| | | | |
|---|---|---|---|
| 4,422,457 A | 12/1983 | Hattori | |
| 5,098,426 A | * | 3/1992 | Sklar et al. ................... 606/5 |
| 5,943,117 A | 8/1999 | Van de Velde | |
| 5,980,513 A | 11/1999 | Frey et al. | |
| 6,030,376 A | * | 2/2000 | Arashima et al. ............. 606/4 |
| 6,312,423 B1 | 11/2001 | Ota et al. | |

FOREIGN PATENT DOCUMENTS

| | | |
|---|---|---|
| DE | 196 18 883 A | 5/1996 |
| EP | 0 960 610 A1 | 12/1999 |
| EP | 1 080 706 A | 3/2001 |
| EP | 1 080 706 A1 | 3/2001 |
| EP | 1 088 523 A1 | 4/2001 |

* cited by examiner

Primary Examiner—John P. Leubecker
Assistant Examiner—Henry M. Johnson
(74) Attorney, Agent, or Firm—Oliff & Berridge, PLC

(57) ABSTRACT

There is disclosed a laser treatment apparatus used for performing treatment on a treatment part of a patient's eye by irradiating the treatment part with a laser beam for treatment. This apparatus includes a treatment beam irradiation optical system for irradiating the treatment beam, the system including a mirror which reflects the treatment beam toward the treatment part; a mirror moving device for moving the mirror to change a point to be irradiated by the treatment beam; and a detector for detecting motion of the mirror.

8 Claims, 7 Drawing Sheets

US 6,673,061 B2

LASER TREATMENT APPARATUS

BACKGROUND OF THE INVENTION

1. Field of the Invention

The present invention relates to a laser treatment apparatus used for performing treatment on a treatment part (an affected part) of a patient's eye by irradiating the treatment part with a laser beam for treatment.

2. Description of Related Art

Many laser treatment apparatuses for use in a photocoagulation treatment or the like have a manipulator for moving a reflection mirror which reflects a laser beam for treatment toward a part to be treated (an affected part) of a patient's eye, i.e., for changing an inclination angle of the reflection mirror. The manipulator is provided in order to allow fine adjustment during alignment of an irradiation point of the treatment laser beam to the treatment part. In a treatment such as panretinal photocoagulation in which the treatment laser beam is irradiated a large number of times to form many photocoagulation spots, a repeat function of periodically irradiating a treatment laser beam while a trigger switch is being pressed is frequently used. This repeat function can be combined with movement (change) of an irradiation point by the manipulator, thereby successively treating a wide area.

However, if laser irradiation is performed during movement of the reflection mirror due to for example the operation of the manipulator at erroneous timings, coagulation spots would be formed in nonuniform shapes and at uneven coagulation density. Consequently, the laser irradiation could not be appropriately executed.

SUMMARY OF THE INVENTION

The present invention has been made in view of the above circumstances and has an object to overcome the above problems and to provide a laser treatment apparatus capable of appropriately performing laser irradiation to allow a satisfactory treatment.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus used for performing treatment on a treatment part of a patient's eye by irradiating the treatment part with a laser beam for treatment, the apparatus including: a treatment beam irradiation optical system for irradiating the treatment beam, the system including a mirror which reflects the treatment beam toward the treatment part; mirror moving means for moving the mirror to change a point to be irradiated by the treatment beam; and detection means for detecting motion of the mirror.

According to another aspect of the present invention, there is provided a laser treatment apparatus used for performing treatment on a treatment part of a patient's eye by irradiating the treatment part with a laser beam for treatment, the apparatus including: a treatment beam irradiation optical system including a mirror which reflects the treatment beam toward the treatment part; a mirror moving mechanism for changing an inclination angle or an arrangement position of the mirror, the moving mechanism including an operation lever; and a sensor for detecting motion of the operation lever.

According to another aspect of the present invention, there is provided a laser treatment apparatus used for performing treatment on a treatment part of a patient's eye by irradiating the treatment part with a laser beam for treatment, the apparatus including: a treatment beam irradiation optical system for irradiating the treatment beam, the system including a mirror which reflects the treatment beam toward the treatment part; an aiming beam irradiation optical system, having an optical axis in a predetermined relation to an optical axis of the treatment beam irradiation optical system, for irradiating an aiming beam by reflecting the aiming beam toward the treatment part by the mirror of the treatment beam irradiation optical system; a mirror moving mechanism for changing an inclination angle or an arrangement position of the mirror; an image pickup device for picking up an image of the treatment part; and a detection unit for detecting motion of the mirror by processing the picked-up image to detect shifting of a point to be irradiated by the aiming beam.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
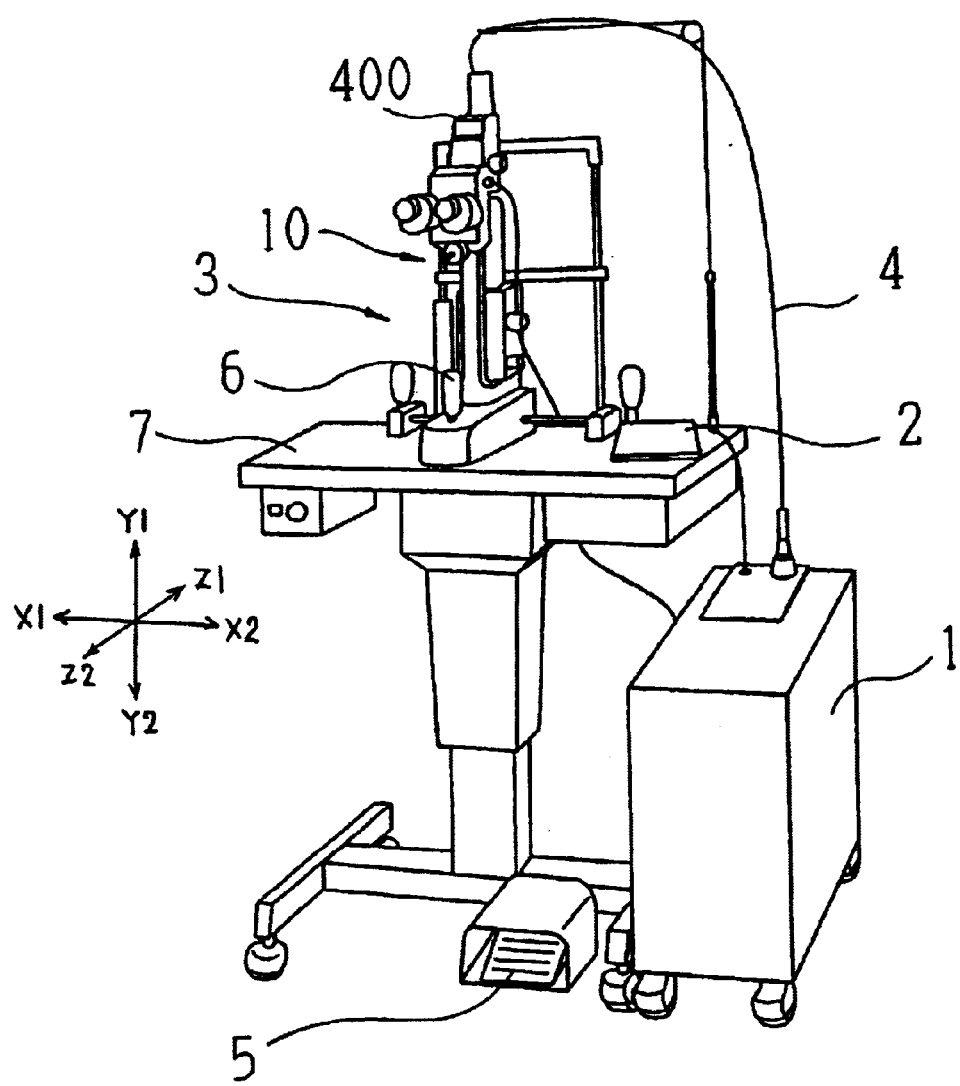
FIG. 1 is a perspective view of a laser treatment apparatus in an embodiment according to the present invention.
Figure 2:
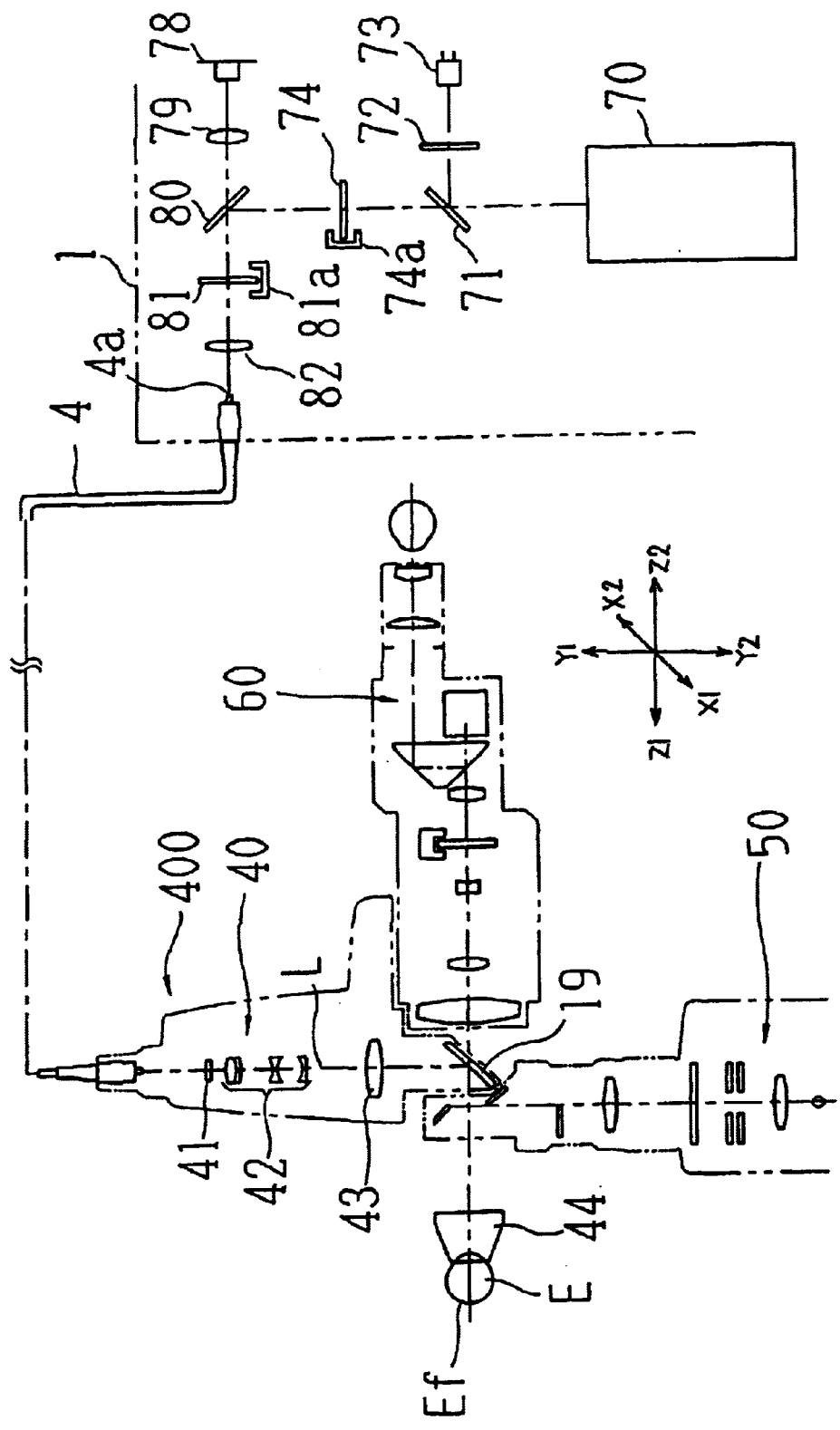
FIG. 2 is a structural view of an optical system of the apparatus.

A detailed description of a preferred embodiment of a laser treatment apparatus embodying the present invention will now be given referring to the accompanying drawings. FIG. 1 is a perspective view of the laser treatment apparatus in the present embodiment. FIG. 2 is a schematic structural view of an optical system of the apparatus. It is to be noted that directions with respect to the apparatus seen from an operator side are defined as follows: a leftward direction is an X1 direction; a rightward direction is an X2 direction; an upward direction is a Y1 direction; a downward direction is a Y2 direction; a forward direction is Z1 direction; and a backward direction is a Z2 direction.

Numeral 1 is a main unit of the laser treatment apparatus, which is internally provided with a laser source 70 which emits a laser beam for treatment (hereafter, simply referred to as a treatment beam), a laser source 78 which emits a laser beam for aiming (hereafter, simply referred to as an aiming beam), and other elements. Numeral 2 is a control unit used for inputting and setting laser irradiation conditions (i.e., irradiation conditions of the treatment beam), output power of the aiming beam, and other conditions. Numeral 3 is a slit lamp delivery provided with an illumination optical system 50 and an observation optical system 60. An irradiation unit 400 is attached to the slit lamp delivery 3. This unit 400 is internally provided with an irradiation optical system 40 for performing laser irradiation (irradiation of the treatment beam) to a patient's eye E. Numeral 5 is a foot switch for generating a laser irradiation command signal (a trigger signal). Numeral 6 is a joystick for moving the slit lamp delivery 3 on a stand table 7.

Numeral 71 is a beam splitter which transmits a large part of the treatment beam and reflects a part of the same. The treatment beam reflected by the beam splitter 71 is made incident to an output sensor 73 via a diffusing plate 72. The output sensor 73 detects the output power of the treatment beam emitted from the laser source 70.

Numeral 74 is a first safety shutter. This shutter 74 is moved out from the optical path by operation of a shutter driving device 91 (see FIG. 4) when the foot switch 5 is pressed to generate the command signal to perform laser irradiation, thus allowing the treatment beam to pass along the optical path. In case of occurrence of abnormal events, the shutter 74 is moved in the optical path to intercept the treatment beam. The opening and closing of the first safety shutter 74 is detected by a shutter sensor 74a.

The aiming beam emitted from the laser source (a laser diode in the present embodiment) 78 passes through a collimator lens 79 and is made coaxial with the treatment beam by a dichroic mirror 80. Numeral 81 is a second safety shutter. The opening and closing of this shutter 81 by a shutter driving device 92 (see FIG. 4) is detected by a shutter sensor 81a. Numeral 82 is a light condensing lens 82 which concentrates each laser beam (the treatment beam and the aiming beam) to an entrance face 4a of an optical fiber 4. Each laser beam is guided through the optical fiber 4 to the irradiation unit 400.

Each laser beam delivered into the irradiation unit 400 passes through a relay lens 41, zoom lenses 42 movable in the optical axis L to change a spot size, and an objective lens 43. Each laser beam is then reflected by a reflection mirror 19 toward the eye E to irradiate a treatment part (an affected part) of the eye E through a contact lens 44. Numeral 50 is an illumination optical system for projecting a slit light to the eye E. This illumination optical system 50 is constructed of an illumination light source, a condenser lens, a slit plate, a projection lens, and others. Numeral 60 is an observation optical system constructed of an objective lens, a variable magnification optical system, a protective filter, an erect prism group, a field diaphragm, an eyepiece lens, and others.

In the irradiation unit 400, there is provided a manipulator 10 for moving the reflection mirror 19 to finely adjust a point to be irradiated (an irradiation point) by each laser beam delivered through the fiber cable 4. In the present embodiment, the mirror 19 is swung by operation of the manipulator 10. In other words, an inclination angle of the mirror 19 is changed. Alternatively, an arrangement position of the mirror 19 may be changed. The manipulator 10 is provided with an operation lever 11 (see FIG. 3) extending backward (in the Z2 direction) of the slit lamp delivery 3.

Figure 3A:
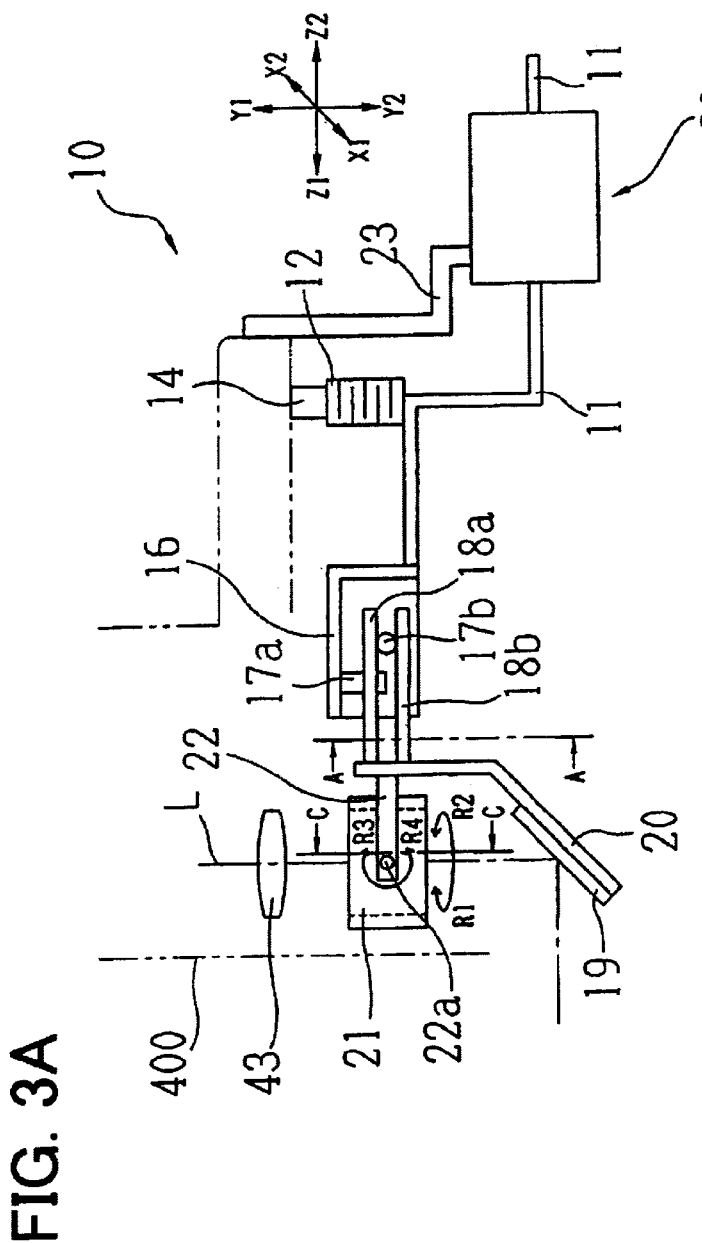
FIGS. 3A to 3C are explanatory view showing a driving mechanism of a manipulator in the apparatus.
Figure 3C:
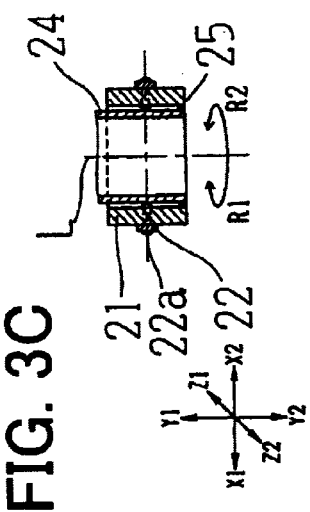
Figure 3B:
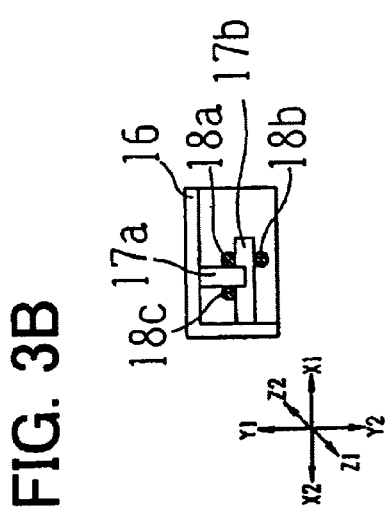

FIG. 3A is an explanatory view of the mechanism of the manipulator 10 seen from the side of the apparatus. FIG. 3B is a sectional view taken on line A—A in FIG. 3A. FIG. 3C is a sectional view taken on line C—C in FIG. 3A.

In a lower end part of the irradiation unit 400, an annular rotation member 21 is held to be rotatable about the optical axis L of the objective lens 43 in directions indicated by arrows R1 and R2. Each laser beam passing through the objective lens 43 is allowed to pass through the interior of the rotation member 21. More specifically, as shown in FIG. 3C, the rotation member 21 is rotatably fit on a pipe 24 via a gear 25. The pipe 24 is fixed to the lower end part of the irradiation unit 400. Thus, each laser beat passes through the interior of the pipe 24. A support member 22 extending backward (in the Z2 direction) is mounted on the peripheral surface of the rotation member 21 with a screw 22a so that the support member 22 is turnable about the screw 22a as a supporting point in directions indicated by arrows R3 and R4. A mirror holding base 20 which fixedly holds the reflection mirror 19 is fixed to the support member 22. Accordingly, the reflection mirror 19 is allowed to swing about the optical axis L in the R1 and R2 directions and to swing about the screw 22a in the R3 and R4 directions. This makes it possible to change an inclination angle of the mirror 19 to change a direction that reflects each laser beam.

The operation lever 11 used for swinging the mirror 19 is provided with a manipulator sensor part 30 for detecting the swing of the mirror 19. The detailed mechanism of the sensor part 30 will be explained later. The lever 11 is partially inserted in a cylindrical member 31 (see FIG. 5) of the sensor part 30 and the cylindrical member 31 is fixed to an arm 23 attached to a rear end of a case configuring the irradiation unit 400. The upper bent portion of the lever 11 is joined to an elastic rubber rod 12 attached to a fixing member 14. This rubber rod 12 is formed with notches on its peripheral surface and in a perpendicular direction to the center axis of the rod, so that the rod 12 can be flexibly bent in the perpendicular direction to the center axis. The fixing member 14 is attached to the inner wall of the case configuring the irradiation unit 400. The joint portion between the lever 11 and the rubber rod 12 functions as a fulcrum of the principle of leverage with respect to the lever 11. It is to be noted that the lever 11 and the arm 23 are actually curved extending front the irradiation unit 400 in order to prevent interference with the case configuring the slit lamp delivery 3. In FIG. 3A, however, the lever 11 and the arm 23 are schematically shown.

An operation transmitting holder 16 is fixed to the lever 11. The holder 16 is provided with a pin 17a extending downward (in the Y2 direction) from an upper wall of the holder 16 and a pin 17b extending leftward (in the X1 direction) from a side wall as shown in FIGS. 3A and 3B. On the upper rear side of the aforementioned mirror holding base 20, three pins 18a, 18b, and 18c are fixedly provided to engage with the pins 17a and 17b. To be more specific, as shown in FIG. 3B, the pins 18a–18c are fixed to the mirror holding base 20 such that the pins 18a and 18c extending in parallel and backward (in the Z2 direction) from the mirror holding base 20 engage with the pin 17a sandwiched therebetween and the pins 18a and 18b extending in parallel and backward (in the Z2 direction) from the mirror holding base 20 engage with the pin 17b sandwiched therebetween.

With the above structure, for example, when the lever 11 is operated downward (in the Y2 direction), the pin 17b is moved with the transmitting holder 16 upward (in the Y1 direction) about the joint portion with the rubber rod 12 as a fulcrum, causing the pin 18a which is one of the pins sandwiching the pin 17b to be pushed upward (in the Y1 direction). This causes the mirror 19 (the mirror holding base 20) to swing about the screw 22a in the R4 direction, thereby turning each laser beam reflected by the mirror 19 in the same downward direction (Y2 direction) as the operating direction of the lever 11. When the lever 11 is operated upward (in the Y1 direction), to the contrary, the mirror 19

(the mirror holding base 20) is swung about the screw 22a in the R3 direction, thereby turning each laser beam reflected by the mirror 19 in the same upward direction (Y1 direction) as the operating direction of the lever 11.

When the lever 11 is operated leftward (in the X1 direction), the pin 17a is moved rightward (in the X2 direction), thereby causing the mirror 19 in conjunction with the mirror holding base 20 and the rotation member 21 to swing in the R2 direction about the optical axis L. As a result, each laser beam is directed leftward (in the X1 direction) corresponding to the operating direction of the lever 11. When the lever 11 is operated rightward (in the X2 direction), to the contrary, the mirror 19 in conjunction with the mirror holding base 20 and the rotation member 21 to swing in the R1 direction about the optical axis L, turning the laser beam rightward (in the X2 direction) corresponding to the operating direction of the lever 11.

When the lever 11 is released from the operator's hand, the lever 11 is normally returned to the center of the cylindrical member 31 by the elasticity of the rubber rod 12. The mechanism of the manipulator 10 is configured such that, when the lever 11 is in the center position (reference position) of the cylindrical member 31, each laser beam reflected by the mirror 19 is irradiated to the center of the observation visual field provided by the observation optical system 60.

Figure 5A:
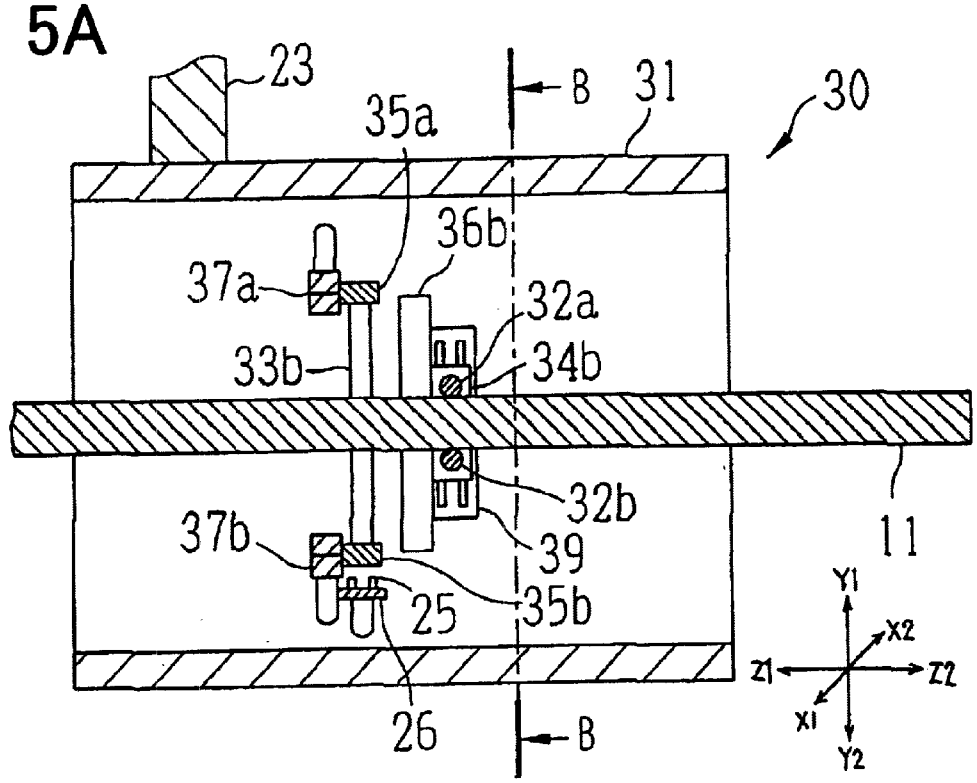
FIGS. 5A and 5B are an explanatory view showing a mechanism of a manipulator sensor part.
Figure 5B:
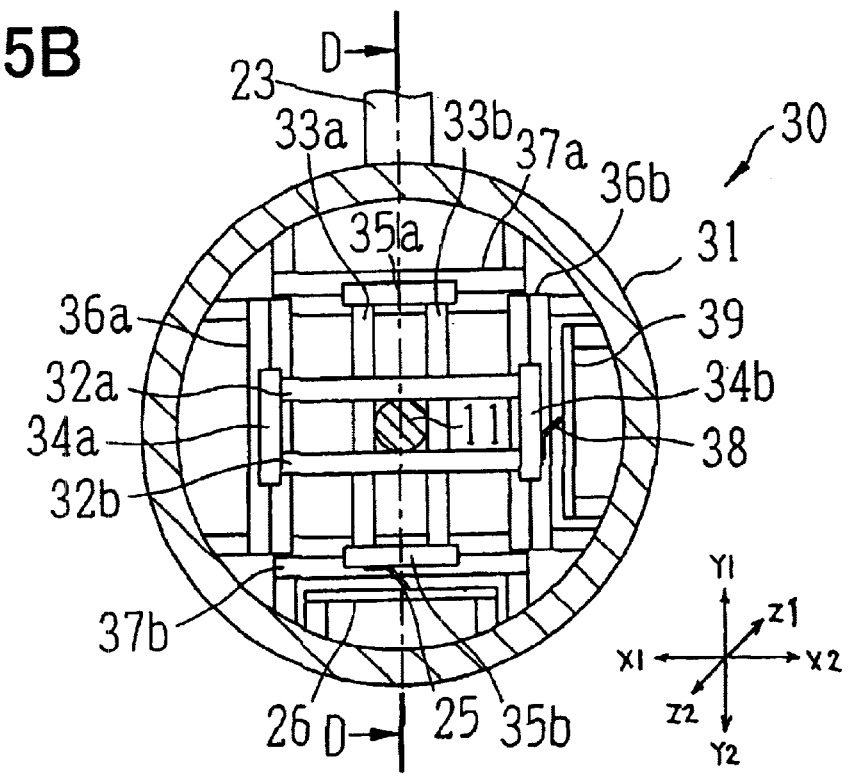

Next, the schematic structure of the manipulator sensor part 30 will be explained with reference to FIGS. 5A and 5B. FIG. 5A is a sectional view of the sensor part 30, showing the internal mechanism thereof. FIG. 5B is a sectional view taken on line B—B in FIG. 5A. Also, FIG. 5A is a sectional view taken on line D—D in FIG. 5B.

In the cylindrical member 31, shafts 32a and 32b are disposed to sandwich the lever 11 from above and below, and shafts 33a and 33b are disposed to sandwich the lever 11 from right and left. Both ends of each of the shafts 32a and 32b are fixed to bases 34a and 34b which are linearly movable on rails 36a and 36b fixedly disposed vertically extending in the cylindrical member 31. An electrically conductive brush 38 is attached to the base 34b and in contact with a resistance surface of a linear potentiometer 39 fixedly provided in the cylindrical member 31. Based on resistance values of the linear potentiometer 39, the displacement of the base 34b, namely, the vertical displacement of the lever 11 can be detected.

Similarly, both ends of each of the shafts 33a and 33b are fixed to bases 35a and 35b which are linearly movable on rails 37a and 37b fixedly disposed horizontally extending in the cylindrical member 31. An electrically conductive brush 25 is attached to the base 35b and in contact with a resistance surface of a linear potentiometer 26 fixedly provided in the cylindrical member 31. Based on resistance values of the linear potentiometer 26, the lateral displacement of the lever 11 can be detected.

Figure 4:
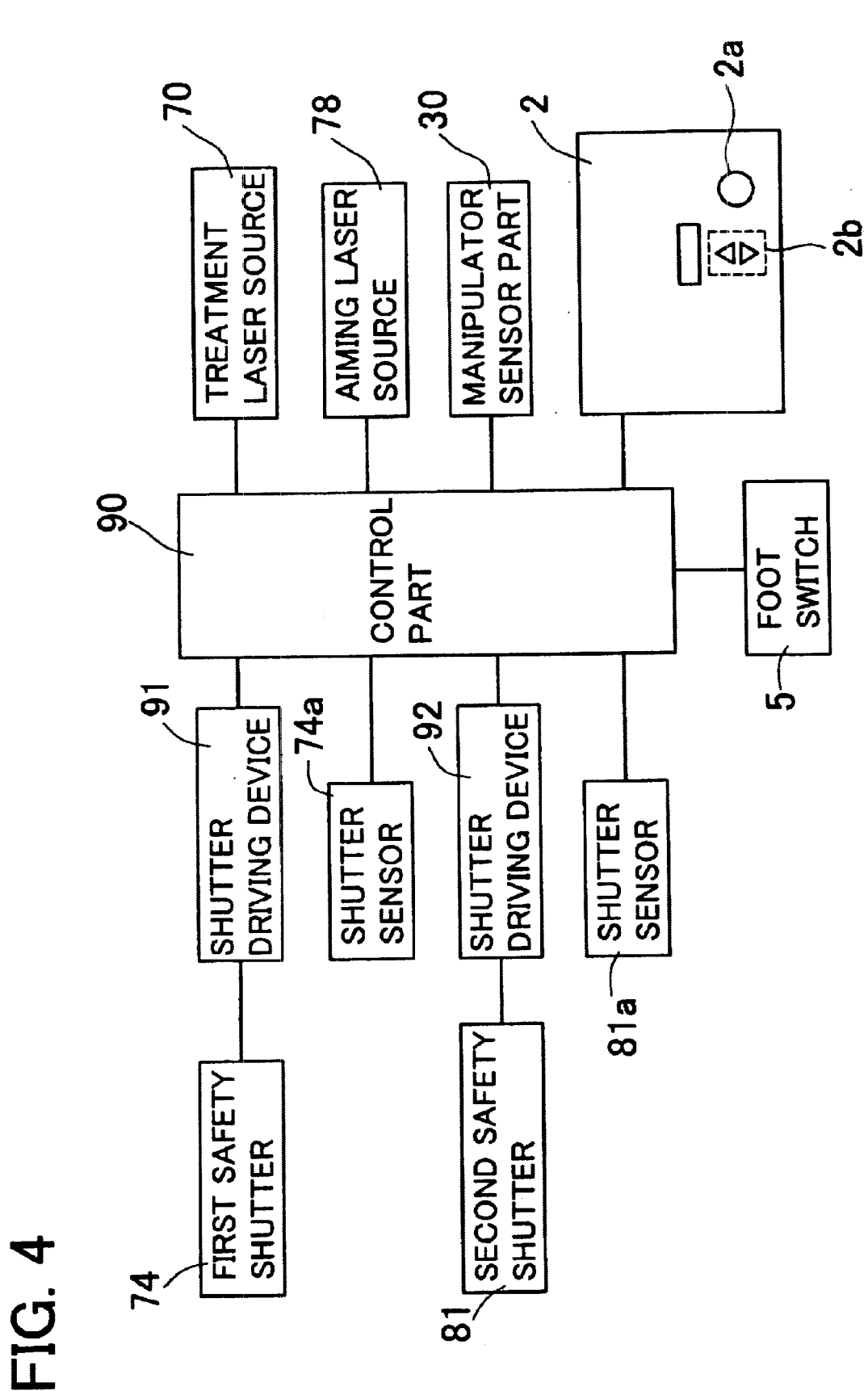
FIG. 4 is a block diagram of a control system of the apparatus.

The operation of the apparatus having the above structure is explained below with reference to a schematic block diagram of a control system in FIG. 4.

For execution of the treatment such as panretinal photocoagulation in which the laser irradiation is performed a large number of times, it is preferable to use the repeat mode of repeatedly irradiating the treatment beam at fixed intervals while the laser irradiation command signal is being input from the foot switch 5. This repeat mode is selected by the switch 2a on the control unit 2. If the repeat mode is not selected, the apparatus goes into a single mode of irradiating the treatment beam only once in response to the laser irradiation command signal from the foot switch 5. In the repeat mode, an interval switch 2b is used to set a time interval for irradiation. For example, if a period of the time interval is set to one second, the treatment beam is irradiated at intervals of one second. A coagulation time, output power, and other laser irradiation conditions are set with unillustrated switches provided on the control unit 2.

Subsequently, the operator observes an eye fundus Ef of the eye E through the observation optical system 60, the eye E being illuminated by the illumination light from the illumination optical system 50. An unillustrated aiming switch is operated to emit the aiming beam. While observing the aiming beam irradiated to the eye fundus Ef, the operator manipulates the joystick 6 and the operation lever 11 of the manipulator 10 to make positional alignment with respect to the treatment part on the eye fundus Ef.

After completion of the positional adjustment of the aiming beam, the foot switch 5 is pressed to generate a laser irradiation command signal. Upon receipt of the command signal, a control part 90 controls the laser source 70 to perform the laser irradiation at intervals of the period previously set with use of the interval switch 2b. To be more specific, for execution of the laser irradiation at the preset intervals in the present embodiment, the control part 90 controls the shutter driving device 91 to open and close the first safety shutter 74 at the preset time intervals. When the treatment beam is irradiated at the preset time intervals, the operator operates the lever 11 according to the time intervals, sequentially moving (changing) an irradiation point on the eye fundus Ef. This motion of the lever 11 is detected by the sensor part 30. Based on signals from the sensor part 30, the control part 90 determines whether or not the lever 11 is in motion, or whether or not the mirror 19 is swinging. To be more specific, this determination is made based on for example the amount of change per unit time in resistance values detected by the linear potentiometers 26 and 39

Figure 6:
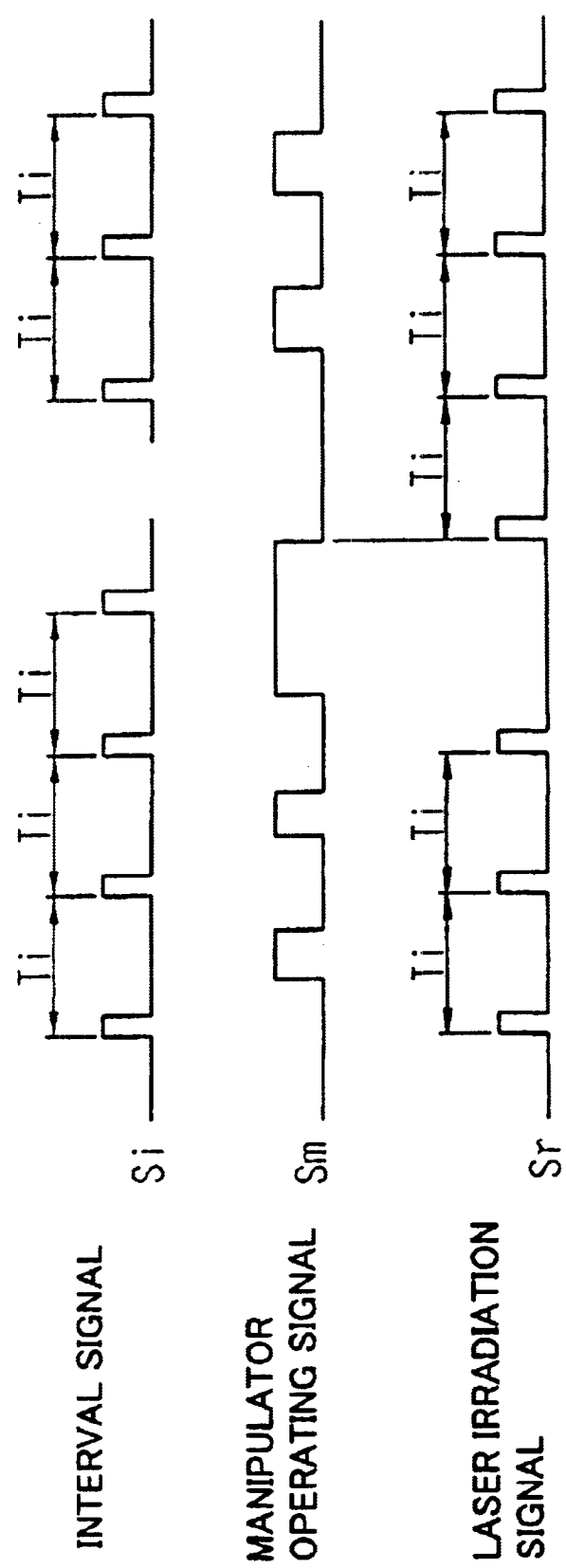
FIG. 6 is an explanatory view showing manipulator operating signals and laser irradiation timings.

As shown in FIG. 6, Ti represents the preset interval period for an interval signal Si. When an operating signal Sm from the sensor part 30 is input during a halt time of the irradiation, the control part 90 controls to perform the laser irradiation in the same timing with the period Ti of the interval signal Si (see Laser irradiation signal Sr in FIG. 6). However, there may occur a case where the operating signal Sm from the sensor part 30 remains input even when the next interval signal Si comes in, in other words, the next interval period comes during operation of the lever 11. In such the case, even when that interval signal comes in, the first safety shutter 74 is held closed to maintain the interception of the treatment beam. Then, when the operating signal Sm from the manipulator sensor part 30 turns off, the first safety shutter 74 is released to enable the laser irradiation. Thereafter, the execution time of this laser irradiation is defined as a restart time and the interval signal Si is then generated at intervals of the period Ti. It is to be noted that stop/release of the laser irradiation may be performed by control of actuation of the laser source 70 itself.

In this manner, the laser irradiation timing is controlled by the control part 90, so that execution of the laser irradiation is prevented while the mirror 19 is swinging. This can prevent a photocoagulation spot from shifting or deviating in a direction corresponding to a mirror moving direction, thus enabling the laser irradiation at uniform irradiation density.

In the above description, the case where the repeat mode is selected is explained. In the single mode, similarly, the laser irradiation is stopped when the swinging of the reflection mirror 19 is detected and the laser irradiation is performed in response to the laser irradiation command signal from the foot switch 5 at the time when the swinging of the mirror 19 is not detected.

The above embodiment is the example of mechanically moving the mirror 19. Alternatively, the mirror 19 may be arranged to be electrically swung by a motor or the like. In this case, the presence/absence of input signal related to the operation lever or an operation switch for swinging the mirror 19 is used to detect whether the mirror 19 is in motion or not.

The mirror 19 may be driven by two or more step motors. In this case, an operation signal of the lever 11 is input in the form of signals of the potentiometers 26 and 39 to the control part 90. In general, the real moving distance of each laser beam is very small. To make it easy to operate the lever 11, therefore, their ratio is set so that the operation amount of the lever 11 is a proportionally amplified amount of the real moving amount of each laser beam. If the mirror 19 is driven by two or more step motors, this ratio may be determined at operator's choice.

Figure 7:
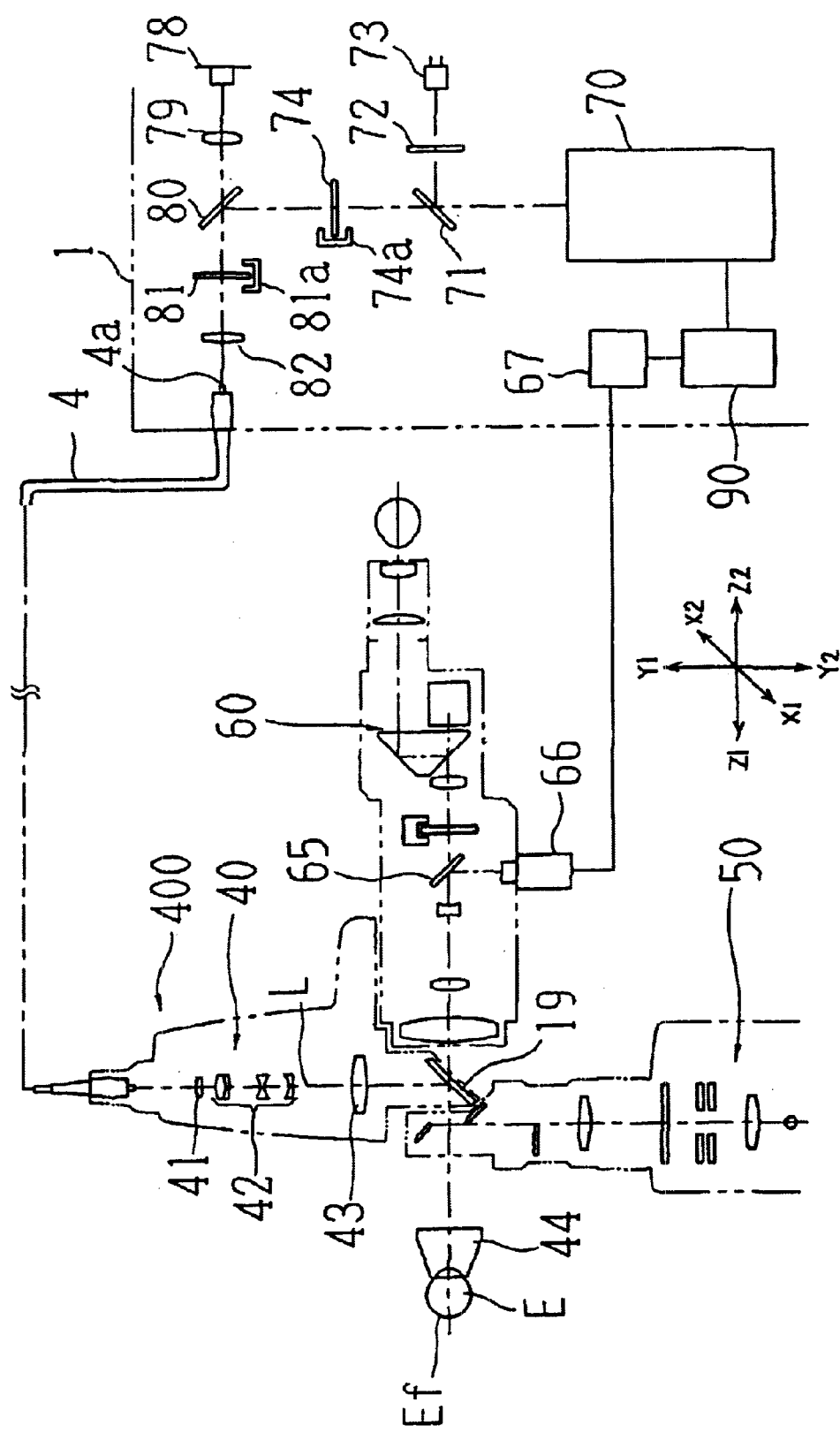
FIG. 7 is a view showing an optical system of an apparatus in a modified example according to the present invention.

FIG. 7 is a structural view of another embodiment of the invention. In this figure, like elements to those in the above embodiment are given like numerals. In FIG. 7, a half mirror 65 is disposed in the optical path of the observation optical system 60. A CCD camera 66 is placed in a direction that the half mirror 65 reflects light. An image signal output from the CCD camera 66 is input to an image processing part 67 in the main unit 1. The image processing part 67 is connected to the control part 90.

The aiming beam irradiated to the eye fundus Ef is observed through the observation optical system 60 and image-picked up, or photographed by the CCD camera 66. The image processing part 67 processes the image signal output from the CCD camera 66 to detect the position of the aiming beam. When the position of the aiming beam has shifted more than an acceptable range per time unit, the control part 90 determines that the mirror 19 is swinging. At this time, the first shutter 74 is moved in the optical path of the treatment beam to interrupt the laser irradiation during movement of the reflection mirror 19.

At the time when the laser irradiation command signal from the foot switch 5 comes in, if it is determined that the aiming beam is moving, that effect may be informed in the form of an alarm or display to the operator to urge him/her to operate the manipulator with stability.

As explained above, according to the present invention, the laser irradiation can be appropriately performed for allowing satisfactory photocoagulation or other treatments.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto.

What is claimed is:

1. A laser treatment apparatus used for performing treatment on a treatment part of a patient's eye by irradiating the treatment part with a laser beam for treatment, the apparatus including:

a treatment beam irradiation optical system for irradiating the treatment beam, the system including a mirror which reflects the treatment beam toward the treatment part;

mirror moving means for moving the mirror to change a point to be irradiated by the treatment beam;

detection means for detecting motion of the mirror;

control means for controlling irradiation of the treatment beam based on detection results by the detection means;

irradiation command signal input means for inputting an irradiation command signal to perform the irradiation of the treatment beam, wherein the control means stops the irradiation of the treatment beam when the detection means detects that the mirror is moving while the irradiation command signal is input: and selection means for selecting a repeat mode in which, during the input of the irradiation command signal, the treatment beam is repeatedly irradiated according to a preset time interval, wherein when the repeat mode is selected, the control means controls the irradiation of the treatment beam based on the detection results by the detection means and at the time interval.

2. The laser treatment apparatus according to claim 1, wherein the mirror moving means includes an operation member which is operated by an operator to move the mirror, and the detection means includes a sensor for detecting motion of the operation member as the motion of the mirror.

3. The laser treatment apparatus according to claim 1, wherein the mirror moving means includes driving command signal input means whereby an operator inputs a driving command signal to move the mirror, and the detection means detects the presence/absence of input of the driving command signal.

4. The laser treatment apparatus according to claim 1, further including an aiming beam irradiation optical system, having an optical axis in a predetermined relation to an optical axis of the treatment beam irradiation optical system, for irradiating an aiming beam by reflecting the aiming beam toward the treatment part by the mirror of the treatment beam irradiation optical system, wherein the detection means includes image pickup means for picking up an image of the treatment part and detects motion of the mirror by processing the picked-up image to detect shifting of a point to be irradiated by the aiming beam.

5. A laser treatment apparatus used for performing treatment on a treatment part of a patient's eye by irradiating the treatment part with a laser beam for treatment, the apparatus including:

a treatment beam irradiation optical system including a mirror which reflects the treatment beam toward the treatment part;

a mirror moving mechanism for changing an inclination angle or an arrangement position of the mirror, the moving mechanism including an operation lever; and a sensor for detecting motion of the operation lever.

6. The laser treatment apparatus according to claim 5 further including a controller for controlling irradiation of the treatment beam based on detection results by the sensor.

7. A laser treatment apparatus used for performing treatment on a treatment part of a patient's eye by irradiating the treatment part with a laser beam for treatment, the apparatus including:

a treatment beam irradiation optical system for irradiating the treatment beam, the system including a mirror which reflects the treatment beam toward the treatment part;

an aiming beam irradiation optical system, having an optical axis in a predetermined relation to an optical axis of the treatment beam irradiation optical system, for irradiating an aiming beam by reflecting the aiming beam toward the treatment part by the mirror of the treatment beam irradiation optical system;

a mirror moving mechanism for changing an inclination angle or an arrangement position of the mirror;

an image pickup device for picking up an image of the treatment part; and a detection unit for detecting motion of the mirror by processing the picked-up image to detect shifting of a point to be irradiated by the aiming beam.

8. The laser treatment apparatus according to claim 7 further including a controller for controlling irradiation of the treatment beam based on detection results by the detection unit.

* * * * *